United States Patent [19]
Allen et al.

[11] Patent Number: 6,113,611
[45] Date of Patent: Sep. 5, 2000

[54] SURGICAL FASTENER AND DELIVERY SYSTEM

[75] Inventors: William J. Allen, Stratford, Conn.; Arnold Miller, Chestnut Hill, Mass.

[73] Assignee: Advanced Vascular Technologies, LLC, Milford, Conn.

[21] Appl. No.: 09/321,077

[22] Filed: May 27, 1999

Related U.S. Application Data

[60] Provisional application No. 60/087,007, May 28, 1998.

[51] Int. Cl.[7] .................................................. A61B 17/04
[52] U.S. Cl. .......................... 606/151; 157/215; 157/216
[58] Field of Search .................................. 606/232, 139, 606/151, 157, 158, 219, 213, 222, 215, 216

[56] References Cited

U.S. PATENT DOCUMENTS

| | | |
|---|---|---|
| 185,606 | 12/1876 | Weston . |
| 380,002 | 3/1888 | Turner . |
| 666,972 | 1/1901 | O'Neal . |
| 798,332 | 6/1905 | Walker . |
| 1,086,258 | 2/1914 | Wilson . |
| 1,451,777 | 4/1923 | Jobst . |
| 1,546,198 | 7/1925 | Brummitt . |
| 2,076,941 | 4/1937 | Faar . |
| 2,508,299 | 5/1950 | Schweikert . |
| 3,120,230 | 2/1964 | Skold . |
| 3,584,628 | 6/1971 | Green . |
| 3,620,212 | 11/1971 | Fannon, Jr. . |
| 3,868,956 | 3/1975 | Alfidi et al. . |
| 3,890,977 | 6/1975 | Wilson . |
| 4,170,990 | 10/1979 | Baumgart et al. . |
| 4,485,816 | 12/1984 | Krumme . |
| 4,505,767 | 3/1985 | Quin . |
| 4,511,081 | 4/1985 | Wilson . |
| 4,512,338 | 4/1985 | Balko et al. . |
| 4,595,007 | 6/1986 | Mericle . |
| 4,612,933 | 9/1986 | Brinkerhoff et al. . |
| 4,634,429 | 1/1987 | Schoettley . |
| 4,669,473 | 6/1987 | Richards et al. ......................... 606/232 |
| 4,671,278 | 6/1987 | Chin . |
| 4,741,330 | 5/1988 | Hayhurst ................................. 606/232 |
| 4,899,744 | 2/1990 | Fujitsuka et al. . |
| 5,002,563 | 3/1991 | Pyka et al. . |
| 5,035,692 | 7/1991 | Lyon et al. . |
| 5,044,540 | 9/1991 | Dulebohn . |
| 5,197,978 | 3/1993 | Hess . |
| 5,207,679 | 5/1993 | Li . |
| 5,219,358 | 6/1993 | Bendel et al. . |
| 5,242,457 | 9/1993 | Akopov et al. . |
| 5,246,443 | 9/1993 | Mai . |
| 5,281,238 | 1/1994 | Chin et al. . |
| 5,358,511 | 10/1994 | Gatturna et al. . |
| 5,447,512 | 9/1995 | Wilson et al. . |
| 5,474,557 | 12/1995 | Mai . |
| 5,573,542 | 11/1996 | Stevens . |
| 5,575,800 | 11/1996 | Gordon . |
| 5,586,983 | 12/1996 | Sanders et al. . |
| 5,601,572 | 2/1997 | Middleman et al. . |
| 5,626,588 | 5/1997 | Sauer et al. . |
| 5,653,759 | 8/1997 | Hogan et al. . |
| 5,716,410 | 2/1998 | Wang et al. . |
| 5,722,981 | 3/1998 | Stevens . |
| 5,741,278 | 4/1998 | Stevens . |
| 5,766,218 | 6/1999 | Arnott . |

FOREIGN PATENT DOCUMENTS 517106  12/1954  Belgium .

*Primary Examiner*—Gary Jackson

[57] ABSTRACT

A surgical fastener preferably made from a shape memory alloy is provided which can access internal tissue or other synthetic material through a small surgical access port or incision. After the fastener is deployed through layers of tissue, it assumes a shape that automatically applies to the layers of tissue an appropriate hemostatic compression which is relatively independent of tissue thickness. The fastener is a suitable replacement for conventional non bio-absorbable sutures and staples in certain clinical applications. Its shape, method of deployment and low force requirements make it suitable for standard surgical procedures and especially suitable for laparoscopic and other less invasive surgery where access to the wound site is limited, including endovascular surgery. A delivery instrument for deploying the fastener is also provided.

12 Claims, 6 Drawing Sheets

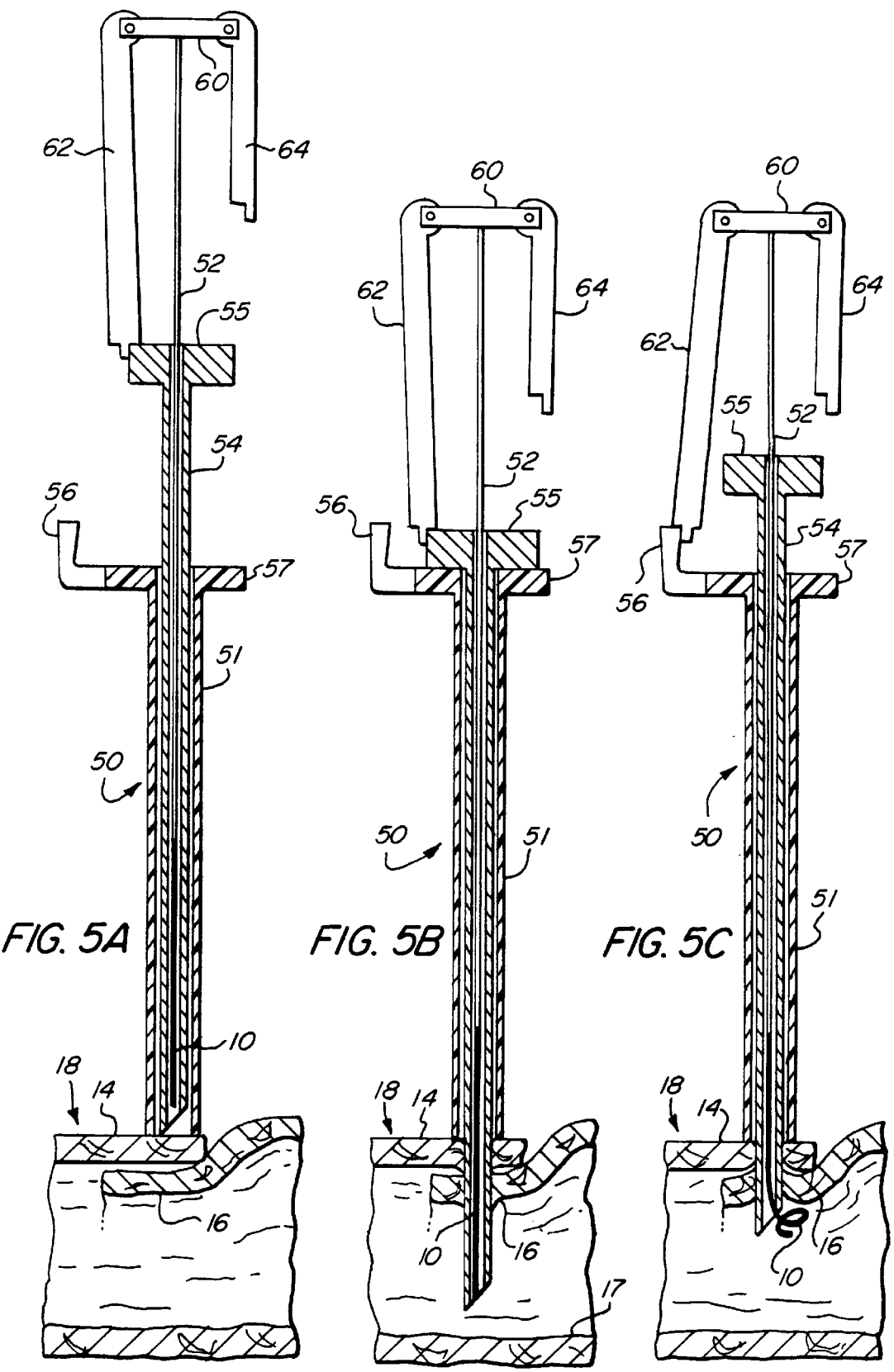

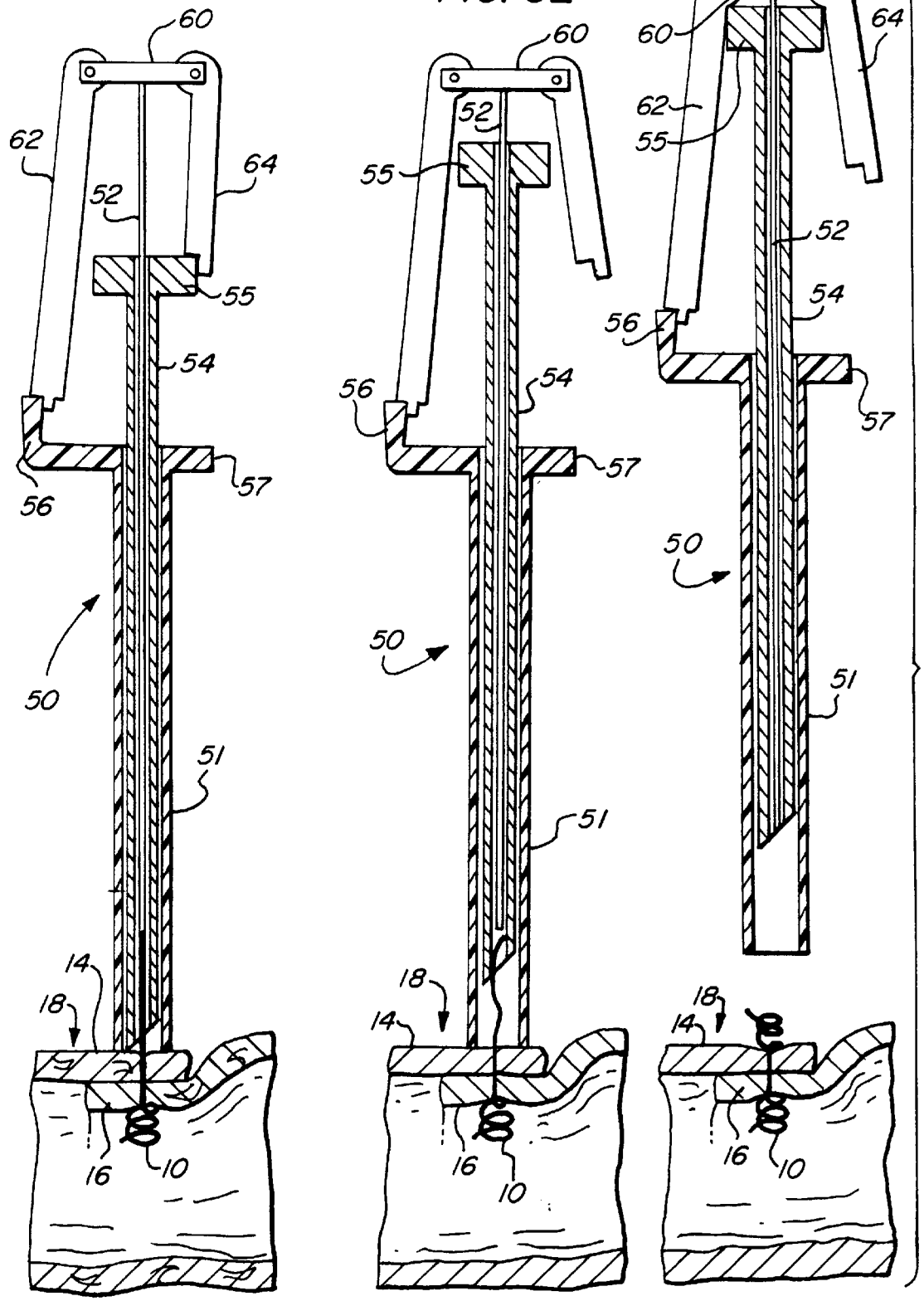

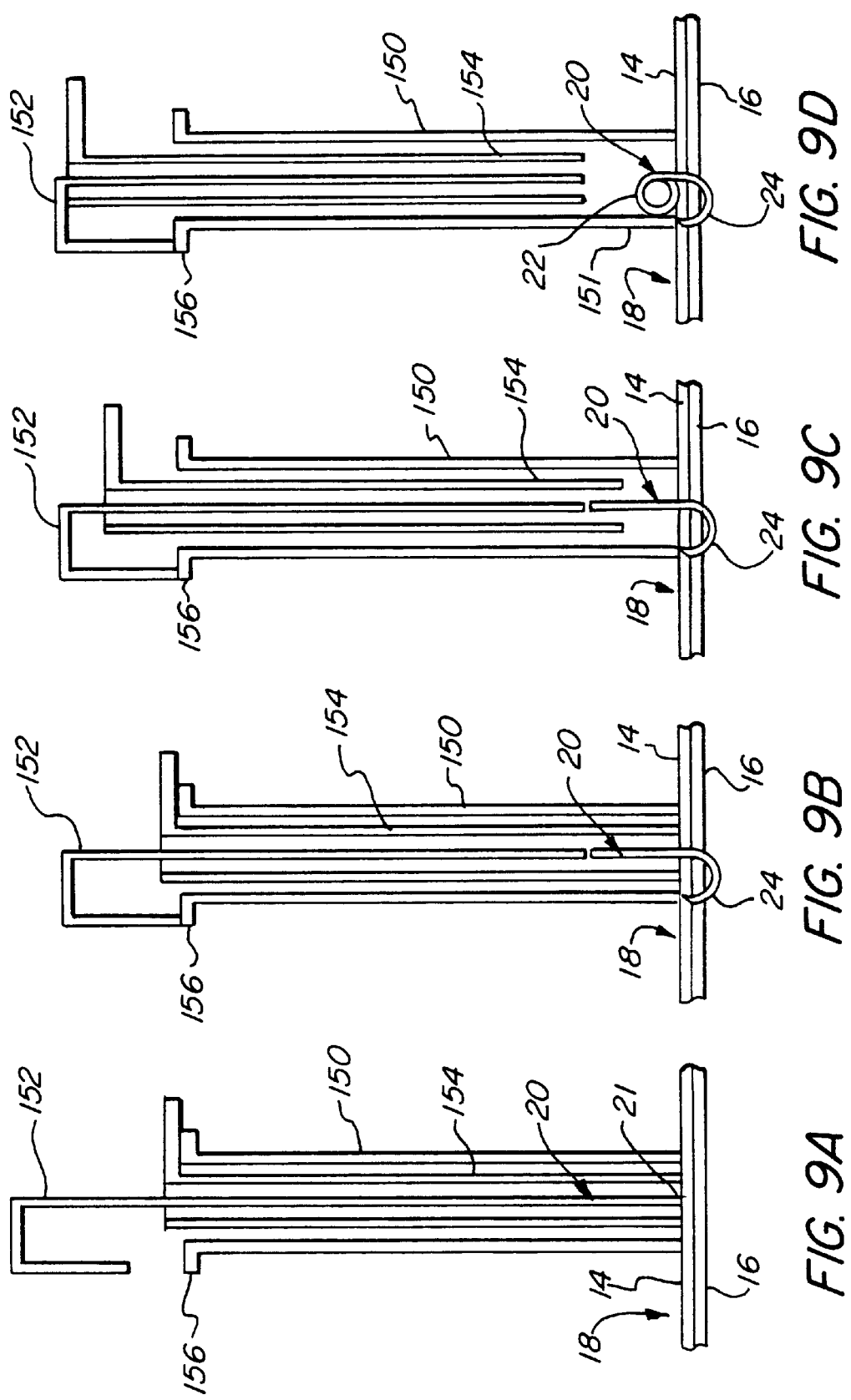

SURGICAL FASTENER AND DELIVERY SYSTEM

This application claims benefit Provisional Appl. 60/087,007 filed May 28, 1998.

FIELD OF INVENTION

The invention relates to a fastener and a deployment instrument for joining multiple layers of thin, flexible material. More specifically, the invention relates to a surgical fastener and a deployment instrument for joining living tissue and/or synthetic materials which may be used as a substitute for tissue.

BACKGROUND OF THE INVENTION

Historically, living tissue has been most commonly surgically repaired by thread, such as a suture, introduced by a pointed metal needle and tied with just enough tension to establish hemostasis or control of bleeding by compressing the tissue. Correct tension is established by the surgeon based on observation and judgment derived from extensive training. Excess tension can cause necrosis (the localized death of living tissue) and eventual failure of the repair.

An alternate method of joining tissue using metal staples has evolved over the last 90 years to a point where specialized staples for both skin and internal tissue closure are in common use today. The staples, which have sharp points for penetrating tissue, are formed in place by delivery instruments which bend them to a permanent shape suitable for tissue retention. The delivery instruments include mechanisms, such as an anvil, which control to some extent the relationship between tissue and staple, including the compression necessary to control bleeding. To the extent that they do so, surgeon skill is less of a factor in successful wound closure.

For conventional surgery, the clinical results for suturing and stapling are essentially the same, but both have their disadvantages. Sutures are suitable for all types of wound closure, but require that the surgeon have adequate access to the wound site and possess the skill to choose and apply the suture correctly. Conventional staples can also be appropriate for internal use, but require that a strong, rigid anvil be placed behind the tissues to be joined. Furthermore, the application of staples requires that there be enough space for an instrument, which can produce the necessary force to form the staple against the anvil. Stapling, however, is generally faster and, as previously noted, requires a lower level of skill.

The recent development of a beneficial, less invasive technique for gall bladder removal has suggested the feasibility of other abdominal procedures, such as bowel and hernia repair, that require the remote application of an internal fastener. As a result, less invasive instruments have been developed for both suturing and stapling remotely from the wound site by the surgeon. At the same time, patient benefit considerations are driving the development of less invasive techniques for a full range of abdominal and thoracic procedures including coronary artery bypass and valve replacement.

To date, stapling has proven to be more suitable for less invasive surgery than suturing. Instruments developed for that purpose approximately replicate the functions of stapler developed for open surgery and are approximately as easy to use. Instruments developed for less invasive suturing, on the other hand, are slow and cumbersome and do not solve the essential problem of tensioning the suture and tying the knot remotely. Sutures will find limited use in less invasive surgery but it is most likely that related wound closure problems beyond the capability of conventional staples will be solved by innovative mechanical fasteners which can more easily be remotely applied.

For instance, a new fastener has been designed for a less invasive hernia repair in which a synthetic mesh is used to reinforce the repair by anchoring it to surrounding tissue. Suturing is feasible but difficult. Conventional stapling is not feasible because an anvil cannot access the distal side of the tissue. The new fastener has the shape of a coil spring with the wire sharpened at one end and has been used successfully to attach the mesh by screwing the coil through it into the tissue. This new fastener can access the wound site through a small port in the abdominal wall. This fastener, however, does not produce compression upon the synthetic and natural tissue layers and thus does not produce hemostasis because the fastener is screwed into the wound site in its natural shape. Because this fastener does not create hemostasis, it may not be suitable for a wide range of surgical applications.

Other surgical fasteners have been fabricated from shape memory alloy. U.S. Pat. No. 4,485,816 to Krumme discloses a shape-memory surgical staple that uses an electric current to heat the staple to make it close. U.S. Pat. No. 5,002,562 to Pyka et al. discloses a fastener made from shape memory alloy that has the shape of a suturing loop in its undeformed shape. As noted above, however, sutures and staples are not always desirable for all surgical application.

It is believed that other applications exist or will be identified for fastening layers of tissue where anvil access is not practical and where compression must be applied to the tissue to achieve hemostasis. For example, these criteria apply to the attachment of a graft more or less at right angles to another, larger, blood vessel ("end to side" anastomosis) such as the aorta for vascular bypass purposes. The availability of a less invasive vascular bypass procedure implies a significant patient benefit. Another example is the use of the fastener in endovascular procedures to attach a graft within large vessels such as the aorta, iliac or femoral arteries to repair aneurysms and occlusions. Stents, which are currently used for this purpose, are often insufficiently compliant to prevent leakage and consequent failure of the repair. Direct fixation of the graft to the inner wall of the vessel by the fasteners described herein may overcome this inherent problem of current techniques for endovascular repair.

What is desired, therefore, is a mechanical fastener and deployment instrument that can access internal tissue through a small surgical access port or incision and that can be applied conveniently and remotely.

SUMMARY OF THE INVENTION

Accordingly, an object of the present invention is to provide a surgical fastener that can access internal tissue through a small surgical access port or incision.

It is a further object of the present invention to provide a surgical fastener that can be applied remotely.

It is yet another object of the present invention to provide a surgical fastener that uses the superelastic properties of a shape memory alloy without having to apply heat to the fastener.

It is still another object of the present invention to provide a deployment instrument that can be used to deploy the surgical fasteners of above.

These objects of the invention are achieved by a surgical fastener preferably made from a shape memory alloy that accesses internal tissue or other synthetic material through a small surgical access port or incision. After the fastener is deployed through layers of tissue, it assumes a shape that automatically applies to the layers of tissue an appropriate hemostatic compression which is relatively independent of tissue thickness. The fastener is a suitable replacement for conventional non bio-absorbable sutures and staples in certain clinical applications. Its shape, method of deployment and low force requirements make it it suitable for standard surgical procedures and especially suitable for laparoscopic and other less invasive surgery where access to the wound site is limited including endovascular surgery. The invention is expected to be especially useful for attaching synthetic grafts to an aorta.

BRIEF DESCRIPTION OF THE DRAWINGS

FIGS. 5A–5F are front cutaway views of a deployment instrument showing the insertion of the surgical fastener of FIG. 1.

FIGS. 9A–9D are side cutaway views showing the use of a deployment instrument with the surgical fastener of FIG. 2.

DETAILED DESCRIPTION OF THE INVENTION

Surgical fasteners, each in accordance with the invention, are shown in FIGS. 1A–4. The surgical fastener is a one piece metal element appropriately configured during manufacture to hold layers of tissue in compression. To apply the fastener, as shown in FIGS. 5A–5F, 6A–6F, and 9A–9D, a straight tube or needle included in a delivery mechanism is preferably used to hold and deflect the fastener from its final shape into a straight configuration. In application, the tube is either inserted through the tissue or held against the tissue to be joined and the fastener is pushed from the tube until the fastener penetrates the tissue and gradually assumes its original shape, trapping and compressing the layers of tissue 18 between its various elements.

In order to straighten the various surgical wire fasteners described herein without permanent deformation, a superelastic alloy of nickel and titanium is preferably used to make the fasteners. The fastener is preferably made from a commercial material Nitinol, which is referred to as a "shape memory alloy." Superelasticity can be conveniently likened to memory. Although forced into a straight line after forming, the superelastic fastener is able to "remember" its former shape and to return to it when no longer constrained within a straight tube. Nitinol in superelastic form has an extremely high elastic limit, which allows large amounts of bending without permanent deformation. In general, Nitinol is capable of strain ratios of up to 8% without experiencing permanent deformation. For round wire, the fastener is designed to function within the limits of d/2R equal to or less than 0.08, where d is the diameter of the wire and R is the radius to which the wire is formed. It should be noted that the fastener described herein can be made from any material so long as it is adequately elastic. Preferably, the material has superelastic characteristics.

Figure 1A:
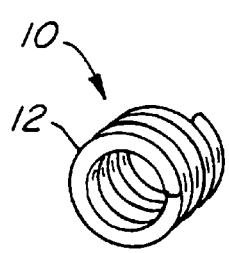
FIGS. 1A, 1B and 1C are an isometric view and two side views, respectively, of the first embodiment of the surgical fastener in accordance with the invention.
Figure 1B:
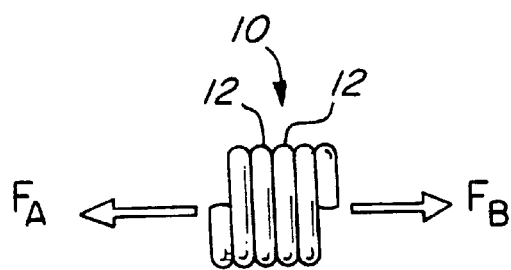
Figure 1C:
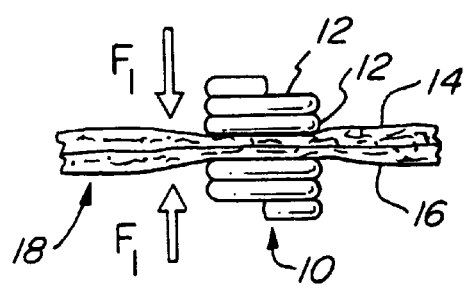

The preferred embodiment of the fastener 10, shown in FIGS. 1A–1C, is essentially that of the body of an extension spring having coils 12. At rest, the coils of this fastener 10 are spring biased towards each other so that a force $F_A$ is required to effect separation of said coils. The force at which the coils just begin to separate is the preload value for the fastener. Additional force causes separation of the coils 12 as a function of the gradient of the fastener. Shown in FIG. 1C, layers of tissue 18 that are trapped between adjacent coils 12 of the fastener will be clamped with a force $F_1$ being substantially normal to the surface of the tissue 18 and having a value somewhat higher than the preload value of the fastener. This force, which is a function of fastener material, dimensions and winding technique, is chosen to insure hemostasis when vascular tissue is to be clamped. It should be noted that a compression spring could be used in place of an extension spring so long as the tissue is thick enough that it is compressed between the coils of the fastener once it is in place. The theory and practice of winding preloaded coils of metallic wire is routinely practiced in the manufacture of extension springs and is well known to those skilled in the art.

When the fastener of FIGS. 1A–1C is made of a superelastic material and the strain ratio limitation described above is observed, the fastener can be straightened to penetrate tissue 18 and then released to allow its coils to reform on both the proximate 14 and distal 16 sides of the tissue thereby clamping the tissue between two coils. The number of coils 12 is not especially critical. At least two full coils 12 are required and more, such as four coils, are preferable to make placement in the tissue less critical. The coils 12 preferably have a diameter of 3/16 to 1/4 of an inch. Preferably, the end of the fastener inside of the body rests flush next to the adjacent coil so that the body will not be injured from the fastener end.

Figure 2:
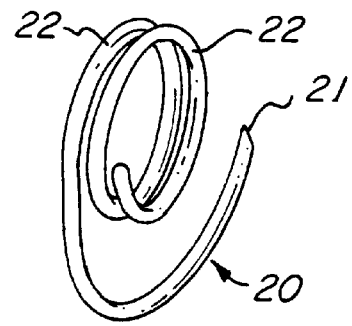
FIG. 2 is an isometric view of the second embodiment of the surgical fastener in accordance with the invention.
Figure 3:
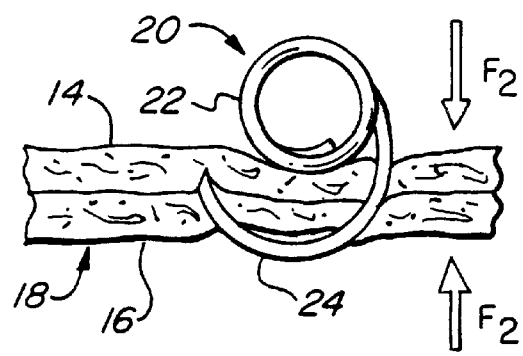
FIG. 3 is a side cutaway view of the second embodiment of the surgical fastener of FIG. 2 in accordance with the invention.

FIGS. 2 and 3 show another embodiment of the fastener 20 before and after installation in two layers 14, 16 of tissue 18. The presence of the tissue layers prevents the fastener from returning completely to its original state. The force required to spread the spring biased fastener apart by this amount therefore also represents the substantially normal compressive force $F_2$ applied to the layers of tissue 18. That force, which is a function of wire diameter and fastener geometry, is chosen by design to achieve homeostasis. Those parameters also determine the gradient or stiffness of the fastener as measured in terms of force $F_2$ versus deflection of the fastener. Since different tissue thicknesses produce different deflections, and therefore different compressive forces, the gradient must be sufficiently low to maintain reasonable hemostasis over the normal range of tissue thickness without inducing necrosis.

FIG. 2 is an isometric view of the fastener 20 shown schematically in FIG. 3. The lower coil 24 penetrates the tissue and curves in a half circle to re-enter the tissue layers. The upper coils 22 bear on the tissue and tend to trap it inside of the larger lower coil. The number of upper coils 22 can vary without altering the essential behavior of the fastener 20. Preferably, two or more coils 22 are used to help distribute clamping forces more uniformly about the lower coil thereby preventing misorientation of the fastener 20 in the tissue 18.

Figure 4:
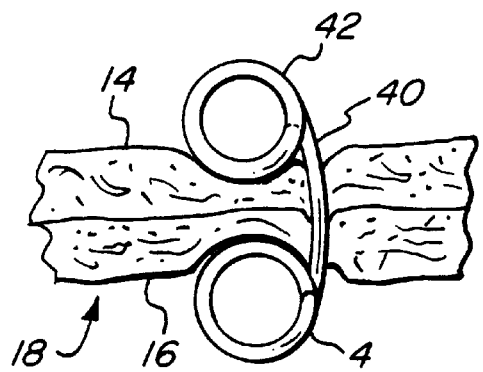
FIG. 4 a side cutaway view of the third embodiment of the surgical fastener in accordance with the invention.

The fastener 40 in FIG. 4 has symmetrical coils to distribute stress uniformly on both sides of the tissues to be joined.

The fasteners in FIGS. 2–3 and 4 are similar to the fastener in FIGS. 1A–1C in that they are spring biased and use coils to apply pressure. The coils in FIGS. 2–3 and 4 each have an axis that is oriented substantially transverse to the direction that the fastener takes when it is in a straightened form, whereas the coils in FIGS. 1A–1C each have an have an axis that is substantially transverse to its straightened form.

The fasteners in FIGS. 1C, 3 and 4 all show a fastener clamping two layers of living tissue 18 which include a proximal layer 14 and a distal layer 16 of tissue. The fasteners described herein, however, can fasten any type of materials together, such as a graft or synthetic fibers which may be used as a substitute for tissue, or a combination thereof. The synthetic fibers, for example, may be a material such as Gore-Tex, Dacron or Teflon. Autogenous and non-autogenous human tissue, as well as animal tissue, may also be used.

For all fasteners described above, the leading end 21 of the fastener, shown in FIG. 2, can be sharpened for ease of penetration either by cutting the wire on a bias or by tapering the end to a sharp point during manufacture of the fastener. The bias cut is commonly used to make sharp points on conventional staples and taper pointing is used to make a certain class of suture needles. Both techniques are well known to those skilled in the art. Other sharpening techniques such as trocar points may also be effectively applied to the fastener. Alternatively or additionally, the tube 154 of the delivery instrument 150 that houses the fastener, as shown in FIGS. 5A–5F and 6A–6F, can have a sharpened tip which is used to penetrate the tissue 18 prior to pushing the fastener from said tube.

A wide variety of fasteners can be designed within the scope of this invention for an equally wide variety of fastening purposes. Some of these shapes are shown in FIGS. 1A–4 and it should be apparent that other variations are both possible and likely as the invention becomes more widely applied.

The surgical fasteners described herein can also be used in applications that require the insertion of a fastener from the interior. For example, the fasteners can be used in endovascular procedures to attach a graft within large vessels such as the aorta or iliac arteries to repair aneurysms or occlusions.

FIGS. 5A–5F show a first embodiment of a deployment instrument 50 and the method for inserting the fastener. The deployment instrument 50 consists of a plunger 52 having a head portion 60, a needle 54 having a head portion 55, and a sleeve 51 having a head portion 57 and a stop 56. The plunger fits slidingly fits inside a lumen of the needle 54, which fits slidingly inside of the sleeve 51. FIGS. 5A–5F show the fastener 10 being used to attach a graft 16 to a blood vessel having a first layer of tissue 14 and an opposite wall 17. The fasteners described herein, however, can be used for any layers of material or tissue. Futhermore, the delivery instrument 50 can deliver any of the fasteners described herein.

Depending on the situation, support for the lower membrane will be required in order to insert the fastener. This will normally be the rigidity of the body tissue itself or a mechanical support which is provided separately, often as an integral part of the instrument that deploys the graft.

For the deployment instrument shown in FIGS. 5A–5D, the head portion 60 of the plunger 52 has two stops attached to it. One stop 62 pivotally engages the head portion 55 of the needle 54 and also pivotally engages the head portion 56 of the sleeve 51. The other stop 64 can engage the head portion 55 of the needle 54. These stops 63, 64 are used to control the amount of depth that the needle and/or fastener may be inserted into the tissue 18.

In FIG. 5A, the deployment instrument is shown ready to insert a fastener 10 into layers of tissue 18 with the tip of the instrument 50 placed against the tissue. First, the stop 62 is engaged against the head portion 55 of the needle such that the needle 54 and plunger 52 can be inserted into the tissue 18 in unison. The needle 54 and plunger 52 are inserted until the head portion 55 of the needle 54 rests upon the head portion 57 of the sleeve 51 as shown in FIG. 5B. It should be apparent that if the needle is inserted into a blood vessel, as shown in FIGS. 5A–5D, care should be taken not to insert the needle past the opposite wall 17 of the vessel.

In FIG. 5C, the stop 62 is swung to engage the stop 62 on the sleeve. This will enable the needle 54 to be raised while the plunger remains still with respect to the plunger 60. While the needle 54 is withdrawn, the restraining force of the needle upon the fastener is removed and the fastener begins to form in its unstressed and undeformed shape.

In FIG. 5D, the needle is raised until its head portion 55 engages stop 64. When the needle 54 engages stop 64, a doctor can be certain that the needle has exited the layers of tissue 18. The lower portion of fastener 10 will now have formed itself in the shape of a coil.

In FIG. 5E, the stop is swung away from the head portion 55 such that the needle 54 of can be withdrawn fully. As shown, the fastener begins to form in its unstressed shape as the needle 54 is removed.

FIG. 5F shows the full withdrawal of the deployment instrument 50. The fastener 10 can now fully assume its unstressed shape. It should be noted that the unstressed coils of the fastener 10 shown in FIGS. 5D through 5F are shown having an exaggerated shape for the sake of clarity. The fastener 10 more accurately would appear as shown in FIG. 1C with the coils exerting a compressive pressure upon the layers of tissue 18.

FIGS. 6A through 6F show a second embodiment of the delivery instrument 100 which can deliver any of the fasteners described herein. The plunger 102 has a head portion 110 having both a short stop 114 and a long stop 112 attached to it. The head portion 55 of the needle 104 has two slots 116 and 118 to accept the long 112 and short 114 stops, respectively, at different times of the process. The needle is slidingly accepted by sleeve 101 having a head portion 107. The tip of the delivery instrument 100, fastener 10 and needle 104 for FIGS. 6A–6F appear the same as in FIGS. 5A–5F, respectively, and are not shown for the sake of clarity.

Figure 6A:
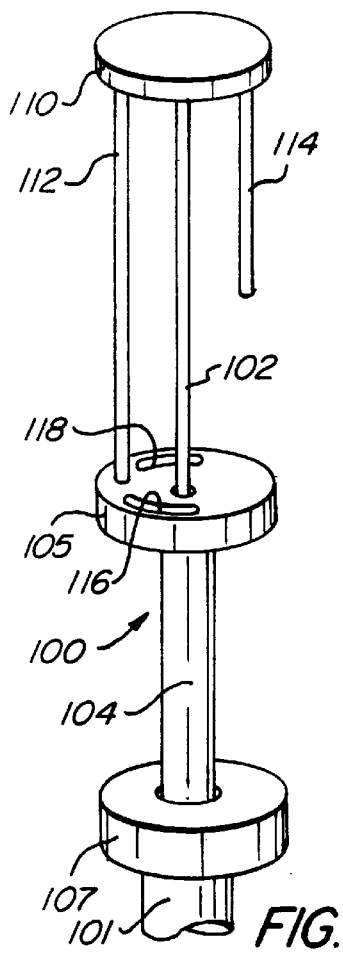
FIGS. 6A–6F are front isometric views of another embodiment of a deployment instrument showing the insertion of a surgical fastener.
Figure 6B:
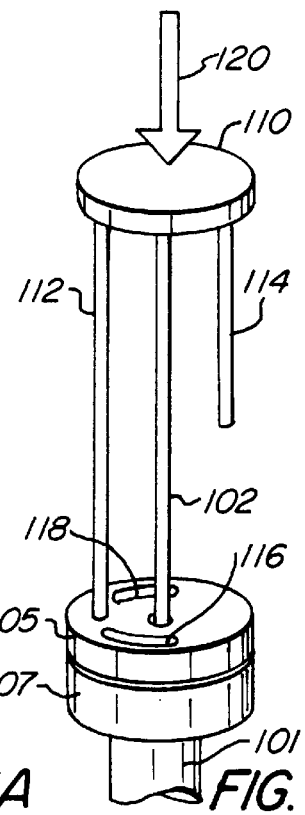

First, as shown in FIG. 6A, the long stop 112 is brought in contact to the head portion 105 of the needle. The plunger 105 and needle 104 are then inserted into the tissue in unison by pushing down in the direction of arrow 120 until the needle's head portion 105 comes into contact with the sleeve's head portion 107 as shown in FIG. 6B. The needle 104 and fastener have penetrated the layers of tissue.

Figure 6C:
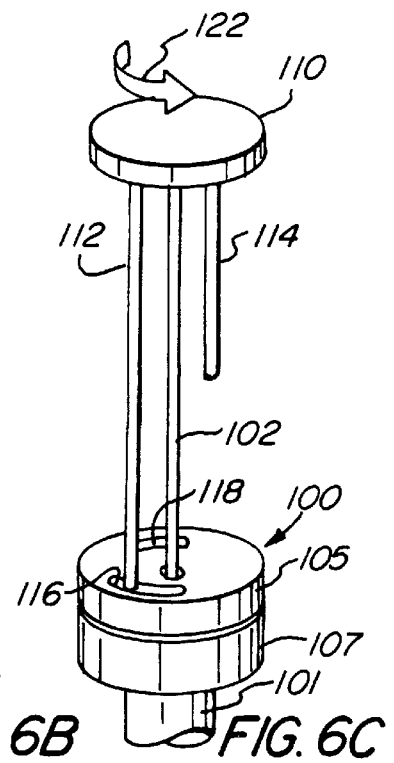
Figure 6D:
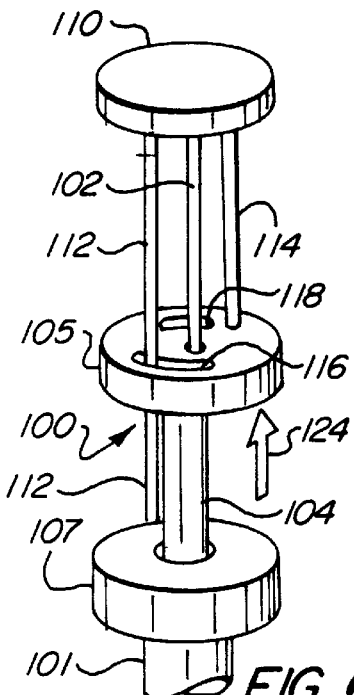

The head portion of the plunger is then rotated as shown in FIG. 6C in the direction of arrow 122 until the long stop 112 can be inserted into slot 116. The needle's head portion 105 is then raised in the direction of arrow 124 until the needle's head portion 105 comes into contact with the short stop 114 as shown in FIG. 6D. In FIG. 6D, the needle 104 will be fully withdrawn from the layers of tissue.

Figure 6E:
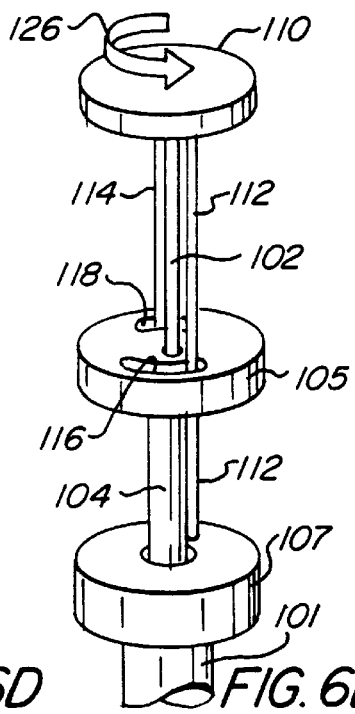
Figure 6F:
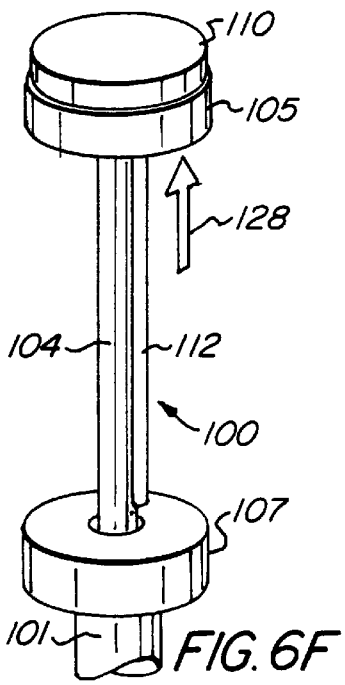

In FIG. 6E, the plunger's head portion 110 is rotated in the direction of arrow 126 until the short stop 114 can be inserted into slot 118. The needle's head portion is then fully raised in the direction of arrow 128 until the head portion 105 comes into contact with the plunger's head portion 110. The needle 104 is now fully retracted from the fastener which should be fastened in the tissue and formed in its unstressed state.

It should be apparent that many types of stops could be used to position the needle 54 and plunger 53 of the deployment instrument 50. For example, the needle could function with only a single stop attached to the shaft of the plunger. Alternatively, visual indicators could also be used, but would be inherently less reliable. It should be apparent that the delivery instrument as shown in FIGS. 5A–5F and 6A–6F could function properly without the short stops 64, 114, but not as reliably. Also, the delivery instrument as shown in FIGS. 5A–5F and 6A–6F could function without the sleeve 51 or 101, respectively. It should be apparent that a plurality of any of these deployment instruments described herein could be integrated in a single deployment instrument for sequential or simultaneous deployment of the fastener.

Figure 7:
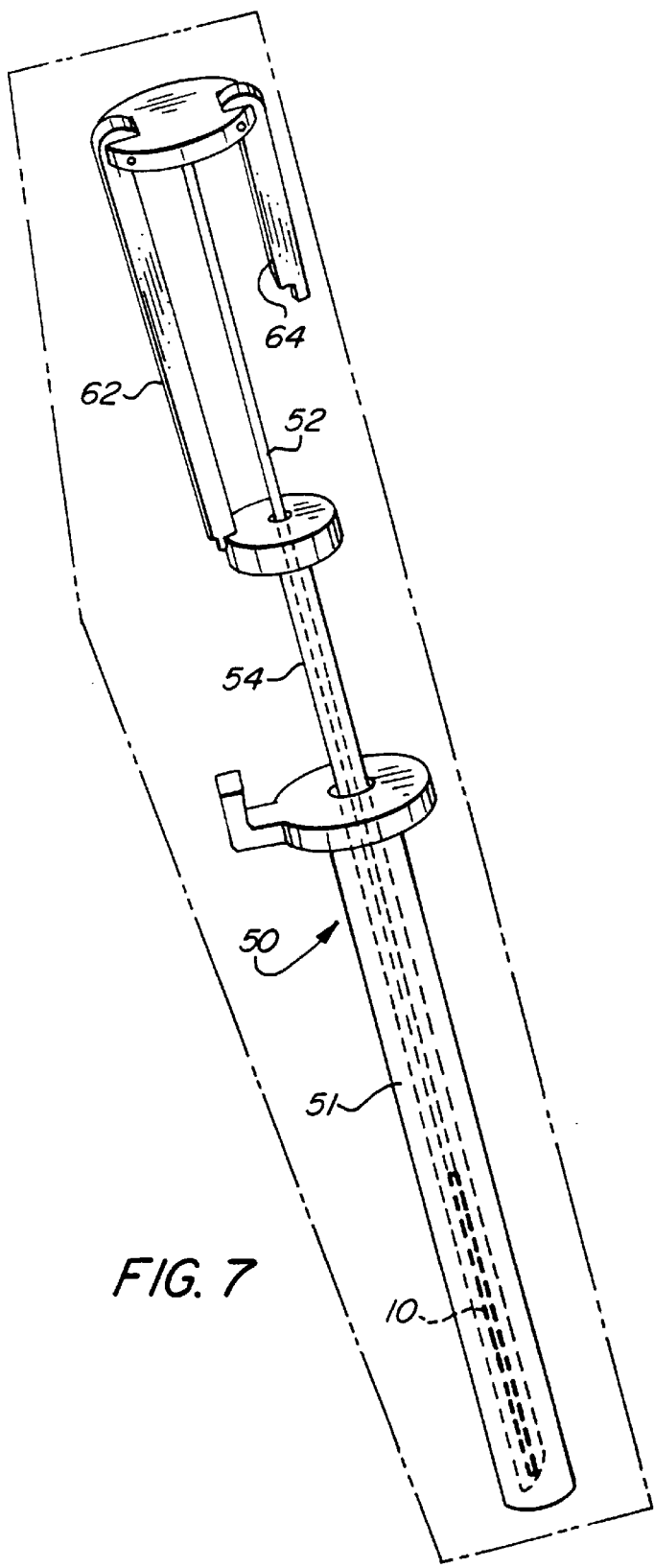
FIG. 7 is a front isometric view of the deployment instrument of FIGS. 5A–5F as it is shipped.

FIG. 7 shows a deployment instrument 50 as it might be shipped from a manufacturer. The surgical fastener 10 preferably is already inserted and straightened inside of the needle 54 for ease of use. The deployment instrument 50 can be shipped with or without the sleeve 51, which can be added later when the fastener is ready to be inserted.

Figure 8:
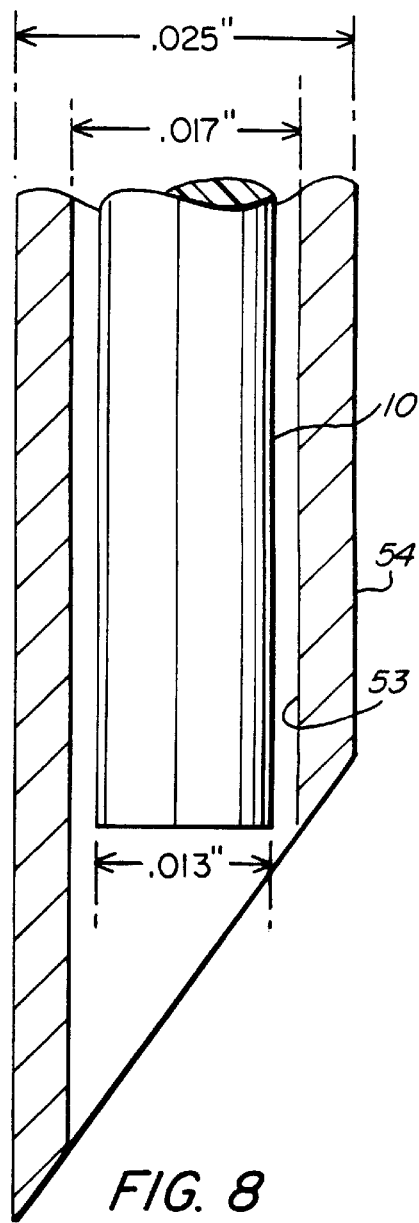
FIG. 8 is a front cutaway view of the deployment instruments of FIGS. 5A–5F and 6A–6F.

FIG. 8 shows an enlarged view of the needle of either FIGS. 5A–5F or 6A–6F with a fastener inside of it. A typical aspect ratio of the length to diameter for this device can be in the order of 40 or 50 for less invasive use. The diameter of the fastener is preferably between 0.012 to 0.014 of an inch, more preferably its diameter is 0.013 of an inch, the inside diameter of the lumen 53 of the needle 54 is preferably 0.017 of an inch and the outside diameter of the needle is preferably 0.025 of an inch.

FIGS. 9A–9D show a third embodiment of the deployment instrument 150 and the method for inserting the fastener. The third embodiment of the deployment instrument 150 is different from the first two embodiments in that the retraining tube 154 is not sharpened to penetrate tissue. Thus, the surgical fastener used with the deployment instrument 150 should have a sharpened end to penetrate tissue. The deployment instrument 150, consisting of slender tubes and rods, is inherently small in diameter compared to its length. Thus, FIGS. 9A–9D are illustrated with a much less favorable aspect ratio for the sake of clarity. A typical aspect ratio of the length to diameter for this device can be in the order of 40 or 50 for less invasive use. It should be apparent that other ergonomically sophisticated designs for the deployment instrument 150 can be envisioned and realized. It should also be apparent that several of these deployment instruments could be integrated in a single deployment instrument 150 for sequential or simultaneous deployment of the fastener.

FIG. 9A shows a deployment instrument 150 resting on layers of tissue 18 to be joined. The deployment instrument 150 restrains a fastener by placing stress upon it. The fastener 20, which in this example is the fastener of FIG. 1, resides in a substantially straightened form entirely within the restraining tube 154. It should be apparent that any of the fasteners described herein if given a pointed end 21 can be used with the deployment instrument of FIGS. 9A–9D. The pointed end 21 of the fastener 20 is facing toward the tissue. A plunger 152 rests on the fastener 20 and is configured to push the fastener partially out of the restraining tube until it stops against shield as in FIG. 9B.

FIG. 9B shows the fastener partially installed by the plunger. As the fastener emerges from its restraining tube it penetrates the proximal 14 and distal 16 layers of tissue and gradually assumes the remembered shape of its lower coil, piercing the distal tissue layer 16 again as it turns upward. The lower coil 24 of the fastener 20, however, preferably remains substantially on the distal side of the tissue. At this point, pusher 152 bears on the shield and can progress no further. Depending on the clinical application, it may be necessary to support the tissue distally during penetration.

FIG. 9C shows restraining tube 154 moving upward, gradually freeing the fastener 20 to assume its remembered shape. It will obviously not able to do so until the restraining tube 154 is completely clear which happens when the restraining tube stops against pusher 152. The restraining tube 154 tends to pull the fastener 20 out of the tissue due to friction producing forces exerted by the fastener on the restraining tube as the former tries to assume its remembered shape. This tendency is offset by the pusher 152 bearing on the upper end of the fastener 20 as the restraining tube 154 moves upward.

FIG. 9D shows restraining tube 154 in its fully upward position as determined by the plunger 152. The restraining tube 154 has cleared the fastener 20 and allowed it to assume its remembered, coiled shape 22, bearing against the tissue 18. The fastener 20 forms within the guide tube 151 suggesting that the guide tube 151, properly shaped, may serve to guide the fastener 20 as it forms above the tissue 18. This may be a useful feature, especially for more complex fasteners which may re-form incorrectly when released from constraint.

The guide tube 151 can serve a dual function as described above, providing a reference stop for plunger 152 and a forming guide for the fastener 20. In some cases the guide tube 151 will not be required.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A surgical fastener for clamping surfaces of a plurality of layers of material together, comprising:

an element having first and second ends and made from a material which enables the element to be transformed from a first stressed elongate shape to a second unstressed shape upon the release of the element from a stressed condition, the first stressed elongate shape of the element enabling its first end to be extended through the plurality of layers of material, and with the second shape of the element being in the form of a spring with a plurality of coils around a spring axis, with the coils being spring biased towards each other along the spring axis with sufficient axial force so as to enable coils on opposite sides of the layers to clamp the layers of material together along the spring axis.

2. The surgical fastener according to claim 1, and further including:
  a hypodermic needle for penetrating said layers and having a lumen sized to slidingly receive the element in its first shape and an externally manipulatable plunger sized to slidingly move through said lumen to advance the element stored therein to a distal end of the needle to enable a distal portion of said element to resume its unstressed coiled shape on the one side of said layers of material when projected from said lumen by the plunger while another portion of said element remains within said lumen in said stressed shape until ejected from said lumen by said plunger on the other side of said layers of material to form an unstressed coiled shape to clamp the layers of material together.

3. The surgical fastener according to claim 1, wherein one of the layers is tissue and wherein said coils are spring biased so as to produce between said coils a sufficiently high compressive hemostasis gripping force when said tissue and said other layer of material are between said pair of adjacent coils to maintain said tissue and said layer of material in sealed contact with each other.

4. A surgical fastener delivery system for securing together a plurality of layers of material, comprising:
  an element having first and second ends and made from a material which enables the element to be transformed from a first substantially straight elongate prestressed wire shape to a second unstressed shape upon a removal of the stress upon the element, the first shape of the element enabling its first end to be extended through the layers of material, and with the second shape of the element including a plurality of spring biased coils around an axis and urged towards each other to provide a clamping force along the axis;
  a restraining tube in the form a hypodermic needle having a lumen sized to slidingly receive the element in its first prestressed elongate wire shape and store the element in said elongate wire shape under said stress; and
  an externally manipulatable plunger sized to slidingly move through said lumen to advance the element stored therein to a distal end of the restraining tube; and
  a stop located on the plunger and oriented so as to to project a predetermined distal portion of the element from the tube after its penetration of the layers of material to enable the formation of a coiled shape on a distal side of the layers of material, whereby emergence of said entire element from the lumen in response to further actuation of said plunger removes said stress upon the element so that it can assume its second coiled shape on a proximate side of the layers of materials and grip the layers of material between coils of the element.

5. A surgical fastener delivery system for securing together a plurality of layers of material, comprising:
  an element having first and second ends and made from a material which enables the element to be transformed from a first substantially straight elongate prestressed wire shape to a second unstressed shape upon a removal of the stress upon the element, the first shape of the element enabling its first end to extend through the layers of material, and with the second unstressed shape of the element including a plurality of spring biased coils around an axis and urged towards each other to provide a clamping force along the axis;
  a restraining tube in the form a hypodermic needle having a lumen sized to slidingly receive the element in its first prestressed elongate wire shape and store the element in said straight shape under said stress; and
  an externally manipulatable plunger sized to slidingly move through said lumen to advance the element stored therein to a distal end of the restraining tube;
  a sleeve to slidingly receive the hypodermic needle and limit its advance there through;
  a first stop located and operative between said sleeve and said hypodermic needle so as to in effect limit advance of said hypodermic needle after it has penetrated the layers of material;
  a second stop element attached to the plunger and operative with respect to said hypodermic needle for projecting a predetermined distal portion of said element from the lumen with a withdrawal of the hypodermic needle while maintaining the position of said plunger to enable the distal projected and unstressed portion of the element to form coils on a distal side of the layers of material with the coils being oriented around an axis that is aligned with the lumen;
  whereby subsequent full withdrawal of the hypodermic needle from said sleeve releases an unstressed proximate portion of said element from the lumen on a proximate side of the layers of material to form coils on said proximate side so that said coils of said unstressed element can clamp the layers of material together.

6. The surgical fastener delivery system of claim 5, wherein the first and second stops are pivotally attached to the plunger.

7. A surgical fastener delivery system for securing together a plurality of layers of material, comprising:
  an element having first and second ends and made from a shape memory alloy that enables the element to be transformed from a first substantially straight prestressed shape to a second shape upon a removal of the stress upon the element, the first shape of the element enabling its first end to penetrate the layers of material, and with the second end of the second shape of the element including a plurality of coils around a spring axis being spring biased toward each other along said spring axis;
  a hypodermic needle having a lumen sized to slidingly receive the element in its first shape and store the element under said stress; and
  an externally manipulatable plunger sized to slidingly move through said lumen to advance the element stored therein to a distal end of the restraining tube; and
  stops located to limit movements of said plunger through said hypodermic needle to obtain a secure and reliable placement of said element after its release from the lumen by the plunger.

8. A method for inserting a surgical fastener into a plurality of layers of material, the steps comprising:
  providing an element having first and second ends and made from a material which enables the element to be transformed from a first substantially straight shape to a second shape upon a removal of stress on the element, the first shape of the element enabling its first end to penetrate the plurality of layers of material, wherein the second shape of the element includes a plurality of coils which are spring biased towards each other along an axis;
  placing the element under stress in a restraining device;
  advancing the first end from the restraining device through the layers of material such that the element projects in an unstressed state to form at least one coil on a distal side of the plurality of layers of material;

withdrawing the restraining device on a proximate side of the plurality of layers of material such that stress from the restraining device is removed and the element transforms from the first shape to the second shape with at least one coil on said proximate side whereby coils at the first and second ends of the element axially press the plurality of layers of material together.

9. The method for inserting a surgical fastener of claim 8, wherein the restraining device is a hypodermic needle, and further comprising the step of penetrating the needle through the layers of material such that the element penetrates the plurality of layers of material.

10. The method for inserting a surgical fastener of claim 9, further comprising the steps of:

guiding the hypodermic needle through a sleeve; and limiting an advance of the hypodermic needle through the sleeve.

11. The method for inserting a surgical fastener of claim 8, further comprising the steps of:

placing a sleeve against a proximate side of the layers of material;

guiding the restraining device with the element through the sleeve and advancing the restraining device through the layers of material sleeve for a predetermined distance determined by the sleeve.

12. The method for inserting a surgical fastener of claim 8, further comprising the steps of:

guiding the restraining device through a sleeve; and limiting an advance of the restraining device through the sleeve.

* * * * *